(12) United States Patent
Wotton, III (10) Patent No.: US 9,681,957 B2
(45) Date of Patent: Jun. 20, 2017

(54) CAGE ASSEMBLY FOR TIBIAL TUBEROSITY ADVANCEMENT PROCEDURE

(71) Applicant: Harold M Wotton, III, Woodstock, CT (US)

(72) Inventor: Harold M Wotton, III, Woodstock, CT (US)

( * ) Notice: Subject to any disclaimer, the term of this patent is extended or adjusted under 35 U.S.C. 154(b) by 0 days.

(21) Appl. No.: 14/442,871

(22) PCT Filed: Nov. 11, 2013

(86) PCT No.: PCT/GB2013/052960
§ 371 (c)(1),
(2) Date: May 14, 2015

(87) PCT Pub. No.: WO2014/076464
PCT Pub. Date: May 22, 2014

(65) Prior Publication Data
US 2015/0335439 A1 Nov. 26, 2015

(30) Foreign Application Priority Data

Nov. 14, 2012 (GB) .................................. 1220467.3

(51) Int. Cl.
*A61F 2/20* (2006.01)
*A61F 2/38* (2006.01)
(Continued)

(52) U.S. Cl.
CPC .............. *A61F 2/389* (2013.01); *A61B 17/68* (2013.01); *A61B 17/8095* (2013.01)

(58) Field of Classification Search
CPC ... A61F 2/28; A61F 2/38; A61F 2/389; A61B 17/8095; A61B 17/8085; A61B 17/80
(Continued)

(56) References Cited

U.S. PATENT DOCUMENTS 8,241,293 B2 * 8/2012 Stone ................... A61B 17/151
606/87
8,790,410 B2 * 7/2014 Kazanovicz ....... A61B 17/8095
623/16.11
(Continued)

FOREIGN PATENT DOCUMENTS

WO  WO 2010/036284  4/2010
WO  WO 2012/075349  6/2012
WO  WO 2012/106323  8/2012

OTHER PUBLICATIONS

GerVetUSA, "Tibial Tuberosity Advancement (TTA)", [retrieved from the Internet Jan. 21, 2014] URL:http://www.germedusa.com/download_pdf/TTA.pdf.
(Continued)

*Primary Examiner* — Alvin Stewart
(74) *Attorney, Agent, or Firm* — Diederiks & Whitelaw, PLC (57) ABSTRACT

A cage assembly for implanting between and securing together two portions of bone in a tibial tuberosity advancement includes an elongated cage body having a first end and a second end, and a securing member. The first end of the cage body and the securing member are engagable with each other so as to interlock in a manner that prevents the securing member from moving longitudinally away from the cage body. The securing member is arrangable, when interlocked with the cage body, such that it has a portion which extends laterally outwards beyond each opposing side of the cage body for use in attaching the securing member to the portions of bone. Different sizes of securing member may be engaged with the cage body. The cage assembly therefore provides a convenient and flexible approach to tibial tuberosity advancement procedures.

21 Claims, 5 Drawing Sheets

(51) Int. Cl.
*A61B 17/80* (2006.01)
*A61B 17/68* (2006.01)

(58) Field of Classification Search
USPC .............. 623/20.32, 20.14, 16.11, 17.16
See application file for complete search history.

(56) References Cited

U.S. PATENT DOCUMENTS

| | | | | |
|---|---|---|---|---|
| 8,920,512 B2* | 12/2014 | Maxson | ............. | A61B 17/8095 623/23.51 |
| 2003/0105526 A1* | 6/2003 | Bryant | ............. | A61F 2/28 623/16.11 |
| 2005/0177245 A1* | 8/2005 | Leatherbury | ...... | A61B 17/7059 623/23.5 |
| 2005/0273114 A1* | 12/2005 | Novak | ............. | A61B 17/15 606/88 |
| 2008/0140213 A1* | 6/2008 | Ammann | ............. | A61B 17/15 623/20.32 |
| 2008/0294260 A1* | 11/2008 | Gray | ............. | A61F 2/4455 623/17.16 |
| 2008/0294262 A1* | 11/2008 | Levieux | ............. | A61F 2/447 623/17.16 |
| 2008/0312742 A1* | 12/2008 | Abernathie | ............. | A61F 2/447 623/17.16 |
| 2009/0082770 A1* | 3/2009 | Worner | ............. | A61B 17/8061 606/60 |
| 2009/0182430 A1* | 7/2009 | Tyber | ............. | A61F 2/4465 623/17.16 |
| 2009/0187247 A1* | 7/2009 | Metcalf, Jr. | ............. | A61F 2/447 623/17.16 |
| 2010/0076564 A1* | 3/2010 | Schilling | ............. | A61B 17/68 623/20.14 |
| 2010/0100186 A1* | 4/2010 | Zubok | ............. | A61B 17/1757 623/17.16 |
| 2010/0131069 A1* | 5/2010 | Halbrecht | ............. | A61F 2/3877 623/20.2 |
| 2010/0137988 A1* | 6/2010 | Markworth | ............. | A61F 2/447 623/17.16 |
| 2010/0198354 A1* | 8/2010 | Halbrecht | ............. | A61B 17/58 623/20.19 |
| 2010/0228296 A1* | 9/2010 | Vraney | ............. | A61F 2/447 606/279 |
| 2010/0249937 A1* | 9/2010 | Blain | ............. | A61B 17/7059 623/17.16 |
| 2011/0040334 A1* | 2/2011 | Kaes | ............. | A61F 2/28 606/279 |
| 2011/0282457 A1* | 11/2011 | Daniele A. | ............. | A61B 17/025 623/17.16 |
| 2011/0301713 A1* | 12/2011 | Theofilos | ............. | A61F 2/447 623/17.16 |
| 2012/0143336 A1* | 6/2012 | Aflatoon | ............. | A61F 2/4465 623/17.16 |
| 2012/0197410 A1* | 8/2012 | Horan | ............. | A61B 17/68 623/20.32 |
| 2013/0060337 A1* | 3/2013 | Petersheim | ............. | A61F 2/447 623/17.16 |
| 2013/0096688 A1* | 4/2013 | Michelson | ............. | A61F 2/442 623/17.16 |
| 2013/0150969 A1* | 6/2013 | Zipnick | ............. | A61F 2/44 623/17.16 |
| 2013/0150977 A1* | 6/2013 | Gabriel | ............. | A61F 2/3859 623/20.32 |
| 2013/0166027 A1* | 6/2013 | Bellas | ............. | A61F 2/447 623/17.16 |
| 2013/0190886 A1* | 7/2013 | Tepic | ............. | A61B 17/56 623/20.32 |
| 2013/0268080 A1* | 10/2013 | Melkent | ............. | A61F 2/442 623/17.16 |
| 2014/0012380 A1* | 1/2014 | Laurence | ............. | A61F 2/4465 623/17.16 |
| 2014/0018922 A1* | 1/2014 | Marino | ............. | A61F 2/447 623/17.16 |
| 2014/0031947 A1* | 1/2014 | Kazanovicz | ............. | A61B 17/8095 623/20.32 |
| 2014/0046447 A1* | 2/2014 | Dunworth | ............. | A61F 2/447 623/17.16 |
| 2015/0335439 A1* | 11/2015 | Wotton, III | ............. | A61B 17/8095 623/20.32 |

OTHER PUBLICATIONS

Kyon, "*Tibial Tuberosity Advancement (TTA)*", [retrieved from the Internet Jan. 21, 2014] URL:http//www.kyon.ch/wp-content/uploads/2012/04/kyon_tta_a4brochure_120409.pdf.

Montavon et al., "*Joint Surgery in Canine Hind Limb—Recent Contributions from the University of Zurich*", European Companion Animal Health, 2006, pp. 25-28.

* cited by examiner

CAGE ASSEMBLY FOR TIBIAL TUBEROSITY ADVANCEMENT PROCEDURE

CROSS-REFERENCE TO RELATED APPLICATION

This application represents a National Stage application of PCT/GB2013/052960 entitled "Cage Assembly for Tibial Tuberosity Advancement Procedure" filed Nov. 11, 2013, pending.

BACKGROUND TO THE INVENTION

The rupture of a cruciate ligament in the knee of a human or other animal is a relatively common injury. Traditionally, such injuries have been addressed by rebuilding or replacing the ruptured ligament. However, if there is an underlying biomechanical or genetic problem that caused the ligament to rupture in the first place then the repaired ligament will be at risk of rupturing again in the future.

In order to solve this problem a procedure known as a tibial tuberosity advancement was developed. Rather than simply rebuilding or replacing the damaged ligament, this procedure seeks to neutralise the forces experienced by the cruciate ligament during motion by changing the angle between the patella ligament and the tibial plateau. This changes the way that the quadriceps muscle and patella tendon pull on the tibia such that the quadriceps muscle and patella tendon pull the tibia back into place, thus taking over the function of the torn cruciate ligament. This procedure is performed by cutting a portion of the tibia comprising the tibial tuberosity from the tibia and then reattaching the tibial tuberosity to the main portion of the tibia with a spacer, known as a cage, arranged between the two portions of bone. The spacer acts to advance the position of the tibial tuberosity forward, hence the name of the procedure being a tibial tuberosity advancement. As the patella tendon naturally extends from the tibial tuberosity, by advancing the tibial tuberosity the positioning of the tendon is altered so that the knee joint can function well.

However, the known cages used for spacing apart the two portions of bone are not particularly versatile. The known cages may therefore be relatively difficult to implant. Also, a relatively large inventory of components may be required in order to cover the range of knee joints in which a cage may be required to be implanted.

It is therefore desired to provide an improved cage assembly for use in tibial tuberosity advancements.

SUMMARY OF THE INVENTION

From a first aspect the present invention provides a cage assembly for implanting between and securing together two portions of bone in a tibial tuberosity advancement, the cage assembly comprising:

an elongated cage body having a first end, a second end, opposing sides, a top and a bottom, the cage body for placement between said two portions of bone such that each side contacts one of said portions of bone so as to maintain a space between the portions of bone; and a securing member;

wherein the first end of the cage body and the securing member are configured to be engagable with each other so as to interlock in a manner that prevents the securing member from moving longitudinally away from the cage body; and wherein the securing member is arrangable, when interlocked with the cage body, such that it has a portion which extends laterally outwards beyond each opposing side of the cage body for use in attaching said securing member to said portions of bone.

The cage assembly of the present invention has a securing member that is separate from the cage body and which is engagable therewith. This allows the cage body to be inserted into the correct location between the portions of tibia bone easily. The securing member may then be subsequently engaged with the cage body and used to secure the cage assembly to the portions of bone. As the securing member is a separate component to the cage body, this allows differently sized or differently configured securing members to be used with the same cage body. This enables the same type of cage body to be fitted in various differently sized and shaped tibias without having to significantly increase the inventory of the surgeon.

The securing member and cage body are preferably releasably engagable such that they may be repeatedly interlocked with and disengaged from each other. This allows the cage assembly to be removed more easily if necessary. Also, it enables the securing member to be replaced with another securing member if necessary.

The cage body preferably comprises a neck portion that extends to a head at the first end of the cage body. The securing member preferably comprises an aperture and the head and aperture are sized and configured such that the aperture may be placed over the head and onto the neck when the securing member is arranged at a first orientation. The securing member may then be rotated about the longitudinal axis of the neck to a second orientation such that the head of the cage body prevents the securing member from being pulled back over the head and away from the cage body. For example, the head and aperture may each have a maximum dimension in one direction that is larger than the maximum dimension in another direction, preferably a perpendicular direction. The neck is preferably smaller than the head in the direction of the larger dimension of the head. In one exemplary embodiment the head and aperture each have a lozenge shape. The lozenge shaped aperture may be placed over the lozenge shaped head and onto the neck of the cage body when their maximum dimensions are aligned with each other. The securing member may then be rotated so that the maximum dimension of the lozenge shaped aperture is perpendicular to the maximum dimension of the lozenge shaped head. As the maximum dimension of the head is larger than the size of the aperture in the direction of the head's maximum dimension (when the securing member has been rotated to the second orientation), the securing member is trapped on the neck of the cage body behind the head and the two components are interlocked. The securing member may then be secured to the portions of tibia on either side of the cage body.

The securing member and cage body may be profiled such that when the securing member is progressively rotated from the first orientation to the second orientation a surface of the securing member engages with a surface of the head, or a surface of another part of the cage body, such that the friction between the two surfaces progressively increases. For example, the two surfaced may be profiled to create a cam action that forces the two surfaces towards each other as they are rotated relative to each other. This helps to interlock the securing member and cage body and may hold the securing member in position whilst it is being secured to the bone portions.

The securing member is preferably substantially plate shaped.

Each portion of the securing member that extends laterally outwards beyond each opposing side of the cage body when the securing member is interlocked with the cage body preferably comprises an opening through which the securing member is screwed or pinned to the bone portions in use. Preferably, the securing member has a central portion with two or more winged portions that comprise the openings. In one arrangement, two winged portions extend in opposite directions away from the central portion. Alternatively, the portion to be secured to each bone may have more than one opening. Other configurations are also contemplated, such as T-shaped securing members that may comprise two openings for securing to one bone portion and one opening for securing to another bone portion. An H-shaped securing member is also contemplated, wherein two openings are provide for securing to each bone portion. Less preferably, no openings are provide and the surgeon screws through these portions to secure them to the bone portions.

The securing member may be rotatable relative to the cage body when interlocked with the cage body so that the positions of the openings may be moved relative to the cage body. This helps adjust the openings to the correct locations adjacent the bone portions so that they can be screwed or pinned in the correct regions of the bone. The securing member may be rotatable in the interlocked position up to +−45 degrees about the neck of the cage body, or up to +−35 degrees, or +−25 degrees.

The cage assembly may comprise a plurality of the securing members, wherein the securing members are of different sizes such that in use each securing member can be attached to said portions of bone at different locations and at different distances from the cage body. The preferred embodiment therefore provides a kit comprising the cage body and a plurality of different securing members. The same kit is then suitable for use with more tibias than if only a single securing member was provided.

The first end of the cage body may have a first substantially planar surface and the second end of the cage body may have a second substantially planar surface, the first and second planar surfaces being parallel to each other and perpendicular to the top and bottom.

Alternatively, the first end of the cage body may have a first substantially planar surface and the second end of the cage body may have a second substantially planar surface, wherein the first and second planar surfaces being angled relative to each other. In this embodiment, the planar surfaces are preferably angled so as to converge towards each other in the direction from the top of the cage body towards the bottom of the cage body. This enables the cage body to be better profiled for use in certain tibias. The substantially planar surface at the first end of the cage body may be substantially perpendicular to the top and bottom of the cage body.

The top and/or bottom of the cage body may be a single continuous rectangle over at least half of the length of the cage body.

The cage body may comprise a box portion arranged towards the first end and a tail portion arranged towards the second end, wherein the tail portion comprises a substantially planar vane member that is connected to the box portion by one or more rod member so as to be spaced apart from the box portion. This configuration provides a relatively long cage body that may be implanted in a relatively large tibia or which may be cut down in length for a smaller tibia by cutting through the rod member so as to remove the vane member. The tail portion preferably comprises one or more additional substantially planar vane members, wherein the vane members are connected together in the tail portion by one or more rod member between each adjacent pair of vane members such that the adjacent vane members are spaced apart from each other. Only a single rod member may connect the vane member to the box portion and/or only a single rod member may connect adjacent pairs of vane members. The single rod member may be located substantially centrally between the top and bottom of the cage body. Alternatively, a single rod member or a plurality of rod members may connect the vane member to the box portion and/or a single rod member or a plurality of rod members may connect adjacent pairs of vane members, wherein each of the rod members is located at a corner between the top and a side of the cage body or between the bottom and a side of the cage body.

Preferably, the first end of the cage body has a first substantially planar surface and each vane member is substantially planar, the planar surface of each vane member being angled relative the first planar surface so as to converge towards each other in the direction from the top of the cage body towards the bottom of the cage body. As the vane members are angled their shape may be optimised for the configuration of the tibia. As each vane member is angled, this optimum shape is maintained even if one or more of the vane members is cut off to reduce the length of the cage body.

The box portion of the cage body preferably has a top wall, a bottom wall, a first end wall at the first end of the cage body and a second end wall towards the second end of the cage body. The first end wall may be angled relative to the second end wall such that the two walls converge towards each other in the direction from the top wall towards the bottom wall. This enables the cage body to provide the optimum shape at the second end if all of the vane members making up the tail portion are cut off.

Each of the top wall and bottom wall of the box portion may be a single continuous rectangle and/or each of the first end wall and second end wall of the box portion may be a single continuous rectangle. The box portion preferably comprises a support member extending from the corner formed between the bottom wall and the second end wall to the corner formed between the top wall and the first end wall; and/or the box portion preferably comprises a support member extending from the corner formed between the bottom wall and the first end wall to the corner formed between the top wall and the second end wall. This configuration is particularly beneficial when the cage member is formed from bioabsorbable material since it allows the cage body to have a relatively small mass and structure that can be absorbed into the animal body relatively quickly, but not before the bone portions have naturally healed in their desired locations.

At least one aperture may extend through the cage body from one side to the other. A material comprising a bone growth stimulating chemical may be arranged in the at least one aperture.

Each side wall of the cage body may be recessed inwards between the top and bottom of the cage body such that when the cage body is positioned between the bone portions only upper and lower regions of the side walls contact the bone portions and not the central regions of the side walls. This configuration minimises the reduction in blood flow around the bone portions that is caused by the presence of the cage body. The animal body is therefore able to heal faster.

Alternatively, or additionally, each of the top and bottom of the cage body may be recessed inwards between the side walls.

The transition between the top and each side of the cage body preferably comprises a smooth curved transition; and/or the transition between the bottom and each side of the cage body preferably comprises a smooth curved transition.

Preferably, the side walls of the cage body are profiled such that if a planar surface was arranged against each side wall the planar surfaces would converge towards each other in a direction from the top to the bottom of the cage body. This allows the portions of bone to extend at the correct angles to each other during healing. The angle between the two converging planar surfaces is preferably about 10 degrees.

The cage assembly may further comprise at least one width adjustment member for altering the width of the cage. A side of the cage body and the width adjustment member may be configured to be engagable with each other so as to interlock in a manner that prevents the width adjustment member moving laterally away from the cage body. Preferably, each side of said cage body is configured to be engagable with and interlock with one of said width adjustment members. This configuration allows the same basic cage body to be widened to a plurality of different sizes by attaching width adjustment members. The width adjustment member or the side of the cage body may comprise a male key, and the side of the cage body or width adjustment member respectively may comprise a female key for interlocking with the male key. The width adjustment member or the side of the cage body may comprise a slot, and the side of the cage body or width adjustment member respectively may comprise a protrusion for interlocking with the slot. Preferably, the slot extends longitudinally along the cage body or width adjustment member and the protrusion is configured to be slid longitudinally into the slot so as to interlock the cage body with the width adjustment member.

Each width adjustment member may be of a tapered wedge shape and configured such that when interlocked with the cage body the combined width of the cage body and width adjustment member tapers from being relatively wide at the top of the cage body to being relatively narrow at the bottom of the cage body. The assembly may comprise a plurality of different width adjustment members having different widths such that when the different width adjustment members are interlocked with the cage body the combined width of the cage body and width adjustment member differs for the different width adjustment members. Alternatively, or additionally, the assembly may comprise a plurality of different width adjustment members having different angles of taper such that when the different width adjustment members are interlocked with the cage body the combined width of the cage body and width adjustment member tapers by different angles for the different width adjustment members.

The cage body and/or securing member may be translucent to X-ray radiation.

The cage body and/or securing member may be made of a polymer or plastic. For example, the polymer or plastic may be poly(L-lactide), poly(D-lactide), polyglycolide, L-lactide and DL-lactide copolymer, L-lactide and glycolide copolymer, L-lactide and caprolactone copolymer, PEEK or PGA. Such material makes it easy for the cage body to be to removed if it becomes necessary. For example, bone or body tissue may have grown into the cage body and then the cage body may be required to be removed due to the presence of an infection. The plastic or polymer cage body may be removed relatively easily by drilling out the cage body.

The plastic or polymer is preferably a bio-absorbable polymer that will be absorbed into an animal body over time when implanted within the animal body.

Preferably, the cage body and/or securing member is impregnated with a bone-growth stimulating chemical and/or a pharmaceutical for promoting healing of the bone portions or tissue of an animal body, the impregnation being such that the chemical and/or pharmaceutical is released into the animal body over time. For example, the bone-growth stimulating chemical may be tri-calcium phosphate. The chemical and/or pharmaceutical may be released as the cage assembly is absorbed into the animal body, in the embodiments in which the assembly is absorbable.

Alternatively, the cage body and/or securing member may be formed from titanium or steel.

The cage assembly cage assembly preferably comprises two or more screws for screwing said securing member into said bone portions.

From another aspect the present invention provides a cage assembly for implanting between and securing together two portions of bone in a tibial tuberosity advancement, the cage assembly comprising:

an elongated cage body having a first end, a second end, opposing sides, a top and a bottom, the cage body for placement between said two portions of bone such that each side contacts one of said portions of bone so as to maintain a space between the portions of bone; and a securing member configured to interlock with the cage body and for securing to said portions of bone;

wherein the cage body comprises a box portion arranged towards the first end and a tail portion arranged towards the second end, wherein the tail portion comprises a substantially planar vane member that is connected to the box portion by one or more rod members so as to be spaced apart from the box portion, and wherein the first end of the cage body has a first substantially planar surface and the vane member is substantially planar, the planar surface of the vane member being angled relative the first planar surface so as to converge towards each other in the direction from the top of the cage body towards the bottom of the cage body.

As described above, the tail portion provides a cage that can be easily cut to down to the desired length if a shorter cage is desired. The cage may comprise multiple angled vane members such that the angle at the second end of the cage body can be preserved by the vane member remaining at the end of the cage body after a vane member has been cut off.

The cage assembly may have any one or combination of the optional features described above in relation to the first aspect of the present invention.

From another aspect the present invention provides a cage assembly for implanting between and securing together two portions of bone in a tibial tuberosity advancement, the cage assembly comprising:

an elongated cage body having a first end, a second end, opposing sides, a top and a bottom, the cage body for placement between said two portions of bone such that each side contacts one of said portions of bone so as to maintain a space between the portions of bone; and a securing member configured to interlock with the cage body and for securing to said portions of bone;

wherein the cage body comprises a box portion arranged towards the first end and a tail portion arranged towards the second end, wherein the tail portion comprises a substantially planar vane member that is connected to the box portion by one or more rod members so as to be spaced apart from the box portion, wherein either:

only a single rod member connects the vane member to the box portion, the single rod member being located substantially centrally between the top and bottom of the cage body; or a rod member connects the vane member to the box portion at each of the four corners of the cage body arranged between the top, bottom and sides of the cage body.

The configuration of the cage assembly enables it to be cut down to size easily, thus avoiding the necessity of the surgeon having multiple length cages in the inventory.

The cage assembly may have any one or combination of the optional features described above in relation to the first aspect of the present invention.

From another aspect the present invention provides a cage assembly for implanting between and securing together two portions of bone in a tibial tuberosity advancement, the cage assembly comprising:

an elongated cage body having a first end, a second end, opposing sides, a top and a bottom, the cage body for placement between said two portions of bone such that each side contacts one of said portions of bone so as to maintain a space between the portions of bone; and a securing member configured to interlock with the cage body and for securing to said portions of bone;

wherein each side wall is recessed inwards between the top and bottom of the cage body such that when the cage body is positioned between the bone portions only upper and lower regions of the side walls contact the bone portions and not the central regions of the side walls.

This configuration minimises the reduction of blood flow around the surfaces of the bone portions due to the presence of the cage body. The arrangement therefore facilitates a faster healing time.

The cage assembly may have any one or combination of the optional features described above in relation to the first aspect of the present invention.

From another aspect the present invention provides a cage assembly for implanting between and securing together two portions of bone in a tibial tuberosity advancement, the cage assembly comprising:

an elongated cage body having a first end, a second end, opposing sides, a top and a bottom, the cage body for placement between said two portions of bone such that each side contacts one of said portions of bone so as to maintain a space between the portions of bone; and a securing member configured to interlock with the cage body and for securing to said portions of bone;

wherein the assembly comprises at least one width adjustment member for altering the width of the cage, wherein a side of the cage body and said width adjustment member are configured to be engagable with each other so as to interlock in a manner that prevents the width adjustment member moving laterally away from the cage body.

The cage assembly may have any one or combination of the optional features described above in relation to the first aspect of the present invention. For example, each side of said cage body is preferably configured to be engagable with and interlock with one of said width adjustment members. The width adjustment member or the side of the cage body may comprise a male key, and the side of the cage body or width adjustment member respectively may comprise a female key for interlocking with the male key. The width adjustment member or the side of the cage body may comprise a slot, and the side of the cage body or width adjustment member respectively may comprise a protrusion for interlocking with the slot. The slot may extend longitudinally along the cage body or width adjustment member and the protrusion may be configured to be slid longitudinally into the slot so as to interlock the cage body with the width adjustment member. Each width adjustment member may be of a tapered wedge shape and configured such that when interlocked with the cage body the combined width of the cage body and width adjustment member tapers from being relatively wide at the top of the cage body to being relatively narrow at the bottom of the cage body. The assembly may comprise a plurality of different width adjustment members having different widths such that when the different width adjustment members are interlocked with the cage body the combined width of the cage body and width adjustment member differs for the different width adjustment members. The assembly may comprise a plurality of different width adjustment members having different angles of taper such that when the different width adjustment members are interlocked with the cage body the combined width of the cage body and width adjustment member tapers by different angles for the different width adjustment members.

From another aspect the present invention provides a cage assembly for implanting between and securing together two portions of bone in a tibial tuberosity advancement, the cage assembly comprising:

an elongated cage body having a first end, a second end, opposing sides, a top and a bottom, the cage body for placement between said two portions of bone such that each side contacts one of said portions of bone so as to maintain a space between the portions of bone; and a securing member configured to interlock with the cage body and for securing to said portions of bone;

wherein the cage body comprises a box portion having a top wall, a bottom wall, a first end wall at the first end of the cage body and a second end wall towards the second end of the cage body, wherein each of the top wall and bottom wall of the box portion is a single continuous rectangle; and wherein the cage body is made of a bio-absorbable polymer that will be absorbed into an animal body over time when implanted within the animal body.

As described above, the configuration of the cage body enables the rate of absorption of the cage body to be optimised such that it is sufficiently low to continue to provide structural support whilst the bone portions heal in their correct locations, but sufficiently high that the assembly does not remain intact in the animal body for a prolonged period of time.

The cage assembly may have any one or combination of the optional features described above in relation to the first aspect of the present invention. For example, the cage body may be impregnated with a bone-growth stimulating chemical and/or a pharmaceutical for promoting healing of the bone portions or tissue of an animal body, the impregnation being such that the chemical and/or pharmaceutical is released into the animal body over time. The box portion may comprise a support member extending from the corner formed between the bottom wall and the second end wall to the corner formed between the top wall and the first end wall; and/or the box portion may comprise a support member extending from the corner formed between the bottom wall and the first end wall to the corner formed between the top wall and the second end wall.

From another aspect the present invention provides a method of performing a tibial tuberosity advancement using a cage assembly as described herein above, the method comprising:

inserting the cage body in a space between a tibial tuberosity and another portion of a tibia bone, wherein the cage body and securing member are interlocked with each other; and screwing or pinning said securing member to said tibial tuberosity and to said another portion of the tibia.

BRIEF DESCRIPTION OF THE DRAWINGS

Various embodiments of the present invention will now be described, by way of example only, and with reference to the accompanying drawings in which.

DETAILED DESCRIPTION OF THE PREFERRED EMBODIMENT

Figure 1A:
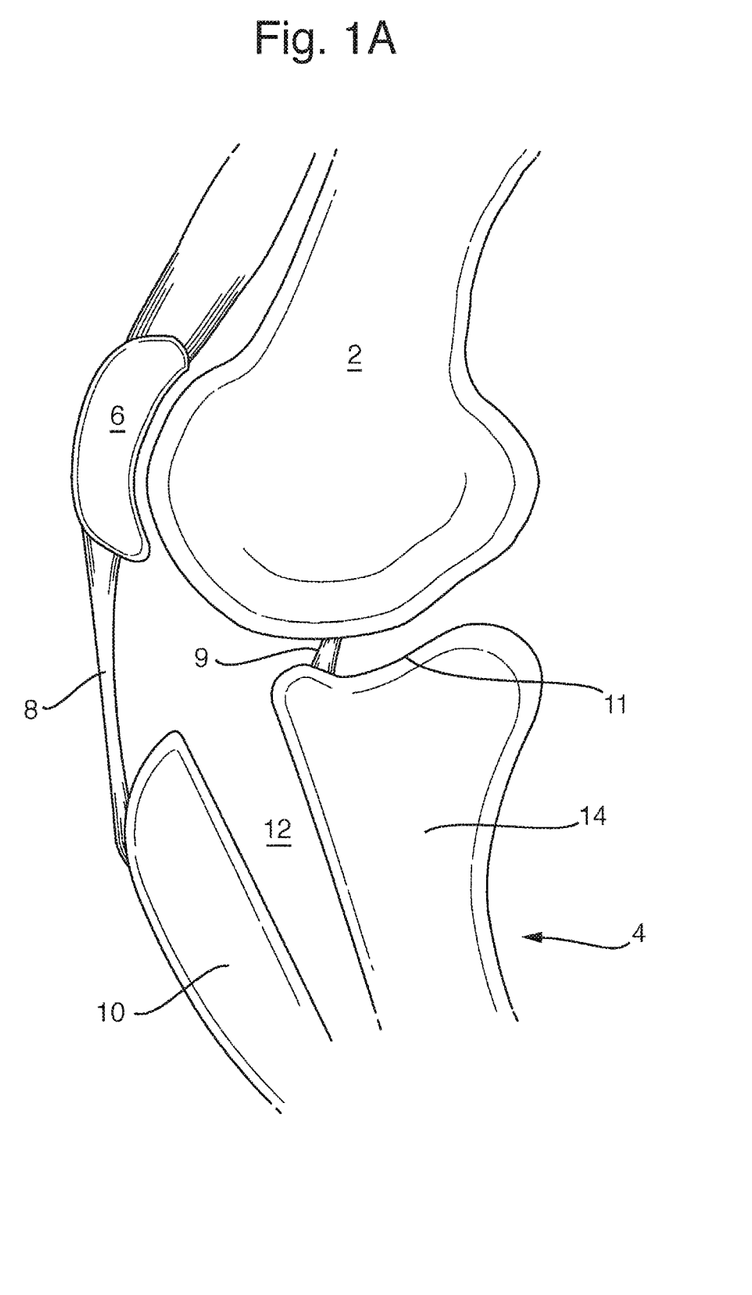
FIG. 1A shows a schematic of a knee joint after the tibial tuberosity has been cut away from the tibia.
Figure 1B:
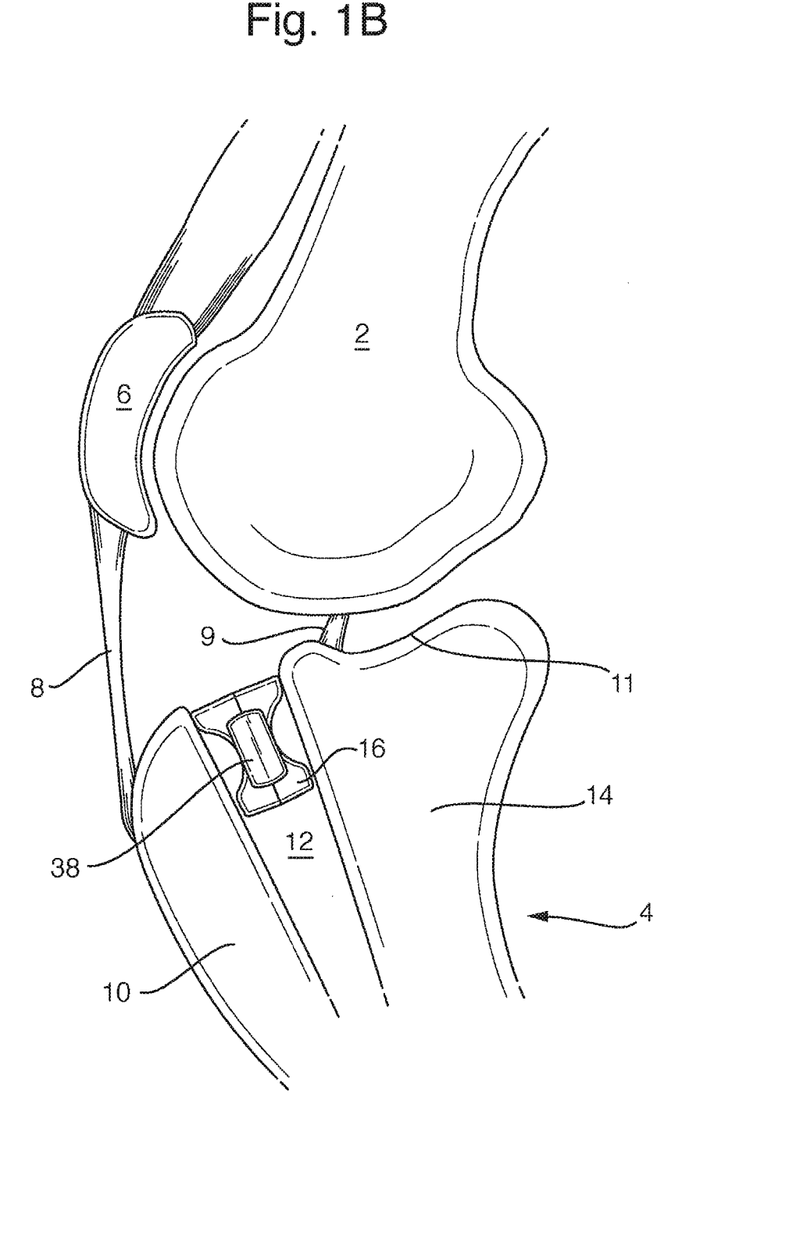
FIG. 1B shows the knee joint when the cage has been arranged between the two portions of tibia.

FIG. 1A shows a cross section of a knee joint that is being subjected to a tibial tuberosity advancement. The view is from the medial side of the knee joint. The knee may be that of a human or another animal, such as a dog. The knee joint is primarily comprised of the femur 2, tibia 4, patella 6, patella tendon 8 and various ligaments. Only a single cruciate ligament 9 is shown in this schematic. As can be seen from FIG. 1A, the procedure involves cutting the tibial tuberosity 10 from the tibia 4 such that a space 12 is provided between the tibial tuberosity 10 and the rest of the tibia 14. The patella tendon 8 remains attached to the patella 6 and the upper region of the tibial tuberosity 10. The lower region of the tibial tuberosity 10 may be connected to the main portion of the tibia 14 by known means. As shown in FIG. 1B, a cage body 16 is then arranged in the space 12 between the tibial tuberosity 10 and the rest of the tibia 14. This cage body 16 maintains the two portions of bone 10,14 at the desired predetermined spacing so that the patella tendon 8 is stretched and arranged to be substantially perpendicular to the tibial plateau 11 so to neutralise the forces exerted within the joint, specifically to the cranial cruciate ligament 9. Different sizes of cage 16 may be used depending on the spacing desired. The cage body 16 is then secured to the tibial tuberosity 10 and the remainder of the tibia 14 so as to hold the portions of bone in the correct position while they heal back together.

Figure 2A:
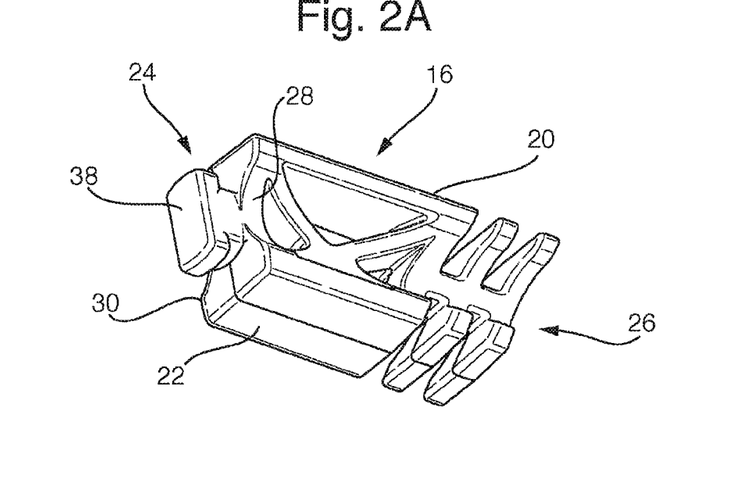
FIG. 2A shows a perspective view of a cage body according to a first embodiment of the present invention.
Figure 2B:
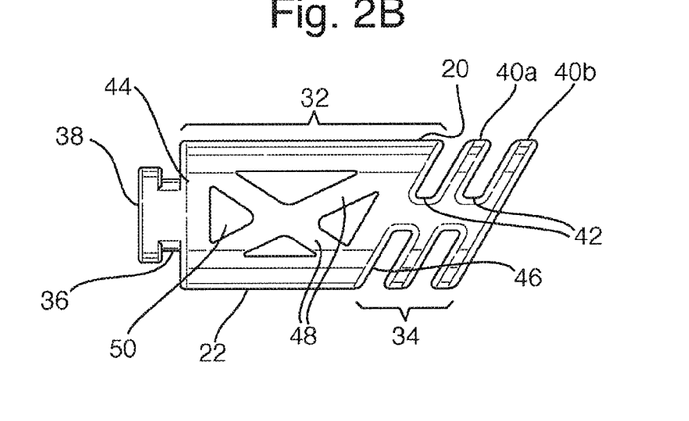
FIG. 2B shows a side view of the cage body.
Figure 2C:
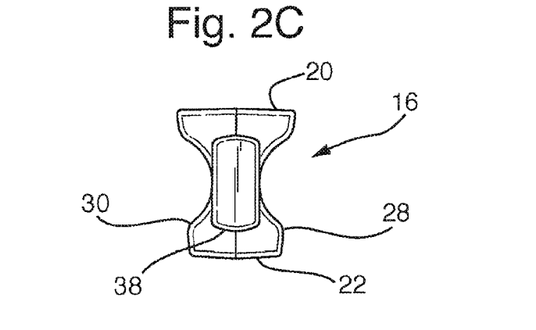
FIG. 2C shows an end view of the cage body.

FIGS. 2A-2C show various different views of a cage body 16 according to a first embodiment of the present invention. The cage body 16 has a top 20, a bottom 22, a first end 24, a second end 26 and two sides 28, 30. The cage body 16 also comprises a box portion 32 located towards the first end 24 of the cage body 16 and a tail portion 34 located towards the second end 26 of the cage body 16. A neck 36 extends from the box portion 32 of the cage body 16 to a head 38. The cage body 16 is arranged in the tibia 4 such that the head 38 protrudes out from between the two portions of bone 10, 14 such that a securing member (not shown) can be placed over the head 38 of the cage body 16 and interlocked therewith. This securing member can then be secured to the portions of bone 10, 14 on either side of the cage body 16 so as to maintain the bone portions 10,14 at the correct spacing whilst they heal. This will be described in more detail below.

The tail portion 34 of the cage body 16 comprises two substantially planar vane members 40a, 40b, although more or less vane members 40 may be provided. Adjacent vane members 40a, 40b are connected each other by a rod member 42 located substantially centrally between the top 20 and bottom 22 of the cage body 16 (shown clearly in FIG. 2B). The box portion 32 is also connected to the adjacent vane member 40a by a rod member 42 located substantially centrally between the top 20 and bottom 22 of the cage body 16. The vane members 40 serve to extend the length of the cage body 16. If it is desired to shorten the length of the cage body 16 prior to use then one or more of the vane members 40 may be cut off by cutting through a rod member 42.

The box portion 32 of the cage body 16 comprises a first end wall 44, a second end wall 46, a top wall 20 and a bottom wall 22. The top and bottom walls 20, 22 are preferably substantially continuous rectangular surfaces. The corner between the top wall 20 and the first end wall 44 is connected by a support member 48 to the corner between the bottom wall 22 and the second end wall 46. Similarly, the corner between the top wall 20 and the second end wall 46 is connected by a support member 48 to the corner between the bottom wall 22 and the first end wall 44. The two support members 48 form a cross shape within the box portion 32 and four apertures 50 through the box portion 32. This configuration of the box portion 32 has been found to be particularly advantageous when the cage body 16 is formed from a bioabsorbable polymer. It is necessary with such polymers to ensure that the cage body 16 is absorbed into the animal body at a rate that is slow enough that the bone portions 10,14 are maintained spaced apart by the cage body 16 by the desired spacing until the animal body has healed enough to maintain the correct spacing. On the other hand, it is not desirable for the cage body 16 to remain intact inside the animal body for a prolonged period of time. The configuration of the box portion 32 provides a relatively small mass of biopolymer that allows the rate of absorption and duration of absorption to be optimised. The configuration also enables material containing bone growth stimulating chemical to be arranged in the apertures 50.

It will be seen from the drawings that the surface at the first end 24 of the cage body 16 is preferably perpendicular to the surfaces of the top and bottom 20, 22 of the cage body 16. This enables the securing member (not shown) to be interlocked with the head 38. In contrast, the surface at the second end 26 of the cage body 16 is angled relative to that of the first end 24 of the cage body 16 such that the two surfaces converge together in a direction from the top 20 to the bottom 22 of the cage body 16. This enables the angle of the second end 26 of the cage body 16 to be optimised for its position within the tibia 4. Each substantially planar vane member 40 and the second end 46 of the box portion 32 is angled at the same angle to the surface at the second end 26 of the cage body 16. This allows the vane members 40 to be cut off to alter the length of the cage body 16 whilst preserving the angled surface at the second end 26 of the cage body 16.

FIG. 2C shows an end view of the cage body 16 looking towards the head 38. As can be seen from this view, each side 28, 30 of the cage body 16 is recessed between the top 20 and bottom 22 of the cage body 16. This ensures that when the cage body 16 is arranged between the two portions 10, 14 of the tibia 4, the amount of cage body 16 in contact with the bone portions 10, 14 is relatively low. As such, the reduction of the blood supply and hence the reduction in bone healing rate caused by the presence of the cage body 16 is minimised. It can also be seen that if a planar surface was arranged against each side 28, 30 of the cage body 16, the two surfaces would converge towards each other in a direction from the top 20 to the bottom 22 of the cage body 16. This configuration is beneficial in providing the angled space 12 between the two portions of bone 10, 14 that is shown in FIG. 1B.

Figure 3A:
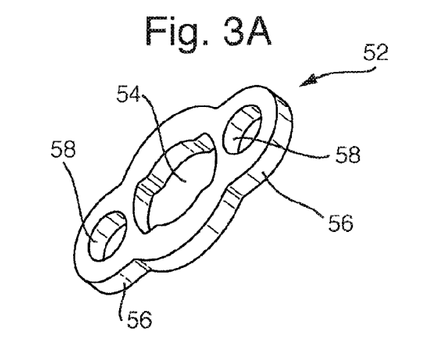
FIG. 3A shows a perspective view of a securing member for interlocking with the cage body of FIGS. 2A-2C and then being secured to the portions of tibia.
Figure 3B:
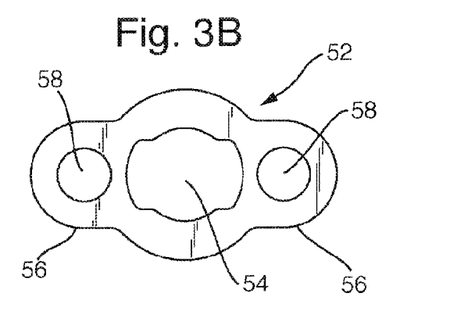
FIG. 3B shows a plan view of the securing member.

FIGS. 3A and 3B show views of the plate-like securing member 52 that is interlocked with the cage body 16 and then secured to the portions of bone 10, 14 on either side of the cage body 16. The supporting member 52 comprises a central aperture 54 that is sized and configured for placing over the head 38 of the cage body 16. The central aperture 54 and head 38 are sized and configured such that the aperture 54 may be pushed over the head 38 and onto the neck 36 of the cage body 16 when the securing member 52 is in a first orientation. The aperture 54, neck 36 and head 38 are also configured such that the securing member 52 may then be rotated about the longitudinal axis of the neck 36 to a second orientation, at which it is interlocked with the cage body 16 and cannot be pulled longitudinally away from the cage body 16. In order to achieve this, each of the head 38 and aperture 54 may have a maximum height that is different to its maximum width. When the securing member 52 is rotated to the second orientation the head 38 is larger than the aperture 54 in the same dimension and so the securing member 52 becomes trapped behind the head 38. The securing member 52 also comprises two winged portions 56 that extend beyond the sides of the cage body 16 when the securing member 52 is rotated to the second orientation. Each of these winged portions 56 comprises an opening 58 that is aligned with one of the portions of tibia 10, 14 on either side of the cage body 16. The securing member 52 is rotatable about the neck 36 of the cage body 16 to a certain degree, such as for example +/−45 degrees, whilst remaining interlocked with the cage body 16. This enables the openings 58 to be rotated to their desired positions against the bone portions 10, 14. When the openings 58 are in the desired positions then screws or pins (not shown) are inserted through the openings 58 and into the portions of bone 10, 14 so as to fix the securing member 52 to the portions of bone. As the securing member 52 is also interlocked with the cage body 16, this maintains the portions of tibia 10, 14 in their correct location relative to each other.

Figure 4A:
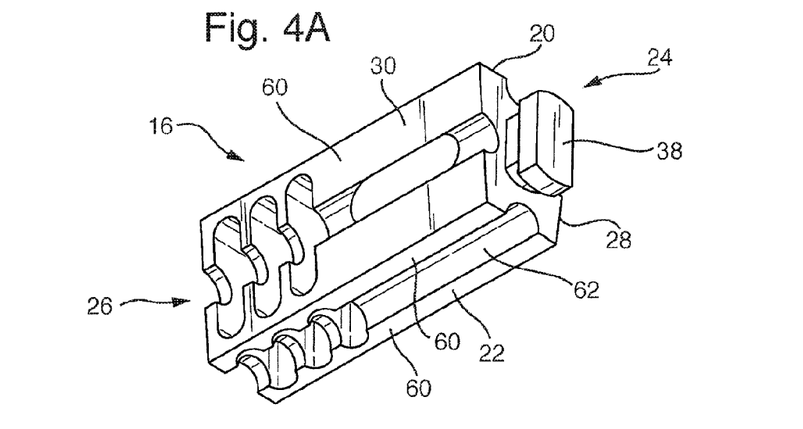
FIG. 4A shows a perspective view of a cage body according to another embodiment of the present invention.
Figure 4B:
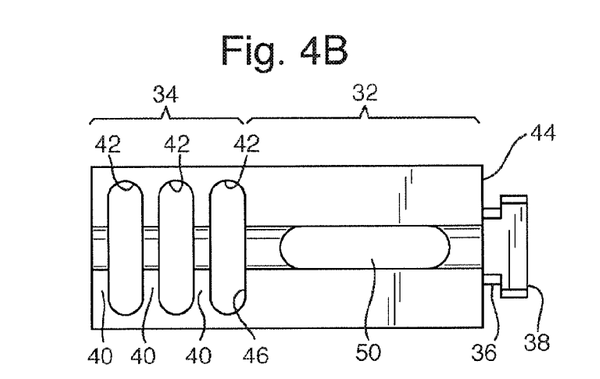
FIG. 4B shows a side view of the cage body.
Figure 4C:
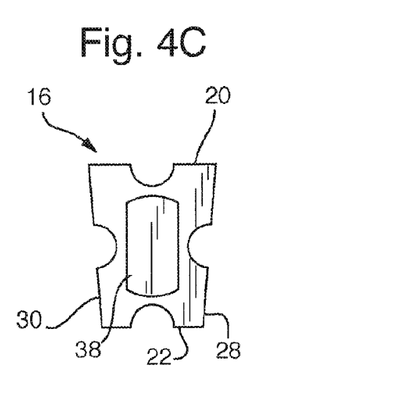
FIG. 4C shows an end view of the cage body.

FIGS. 4A to 4C show views of a second embodiment of a cage body. The cage body is similar to that described above in relation to FIGS. 2A to 2C and like portions have been designated with the same reference numerals. The cage body 16 of the second embodiment has a box section 32 formed from four longitudinal rods 60 that form the top 20, bottom 22 and sides 28, 30 of the box portion 32. The rods 60 are spaced apart over the width and height of the box portion 32 so as to form a slotted aperture 50 through the box portion 32 from one side 28 to the other 30 and also to form a slotted aperture 62 through the box portion 32 from the top 20 to the bottom 22. The tail portion 34 is formed from substantially planar vane members 40 that are parallel with the first end 44 of the box portion 32 and perpendicular to the top 20, bottom 22 and sides 28, 30 of the cage body 16. Adjacent vane members 40 are interconnected with each other by rod members 42 arranged at the corners of the cage body 16. Similarly, the box portion 32 is interconnected with the adjacent vane member 40 by rod members 42 arranged at the corners of the cage body 16. This embodiment is particularly advantageous for cage bodies made from biocompatible metal such as titanium. The locations of the rod members 42 at the corners of the cage body 16 enable them to be cut through relatively easily, even though they are metal, when the tail portion 34 is being cut to the desired length.

Figure 5A:
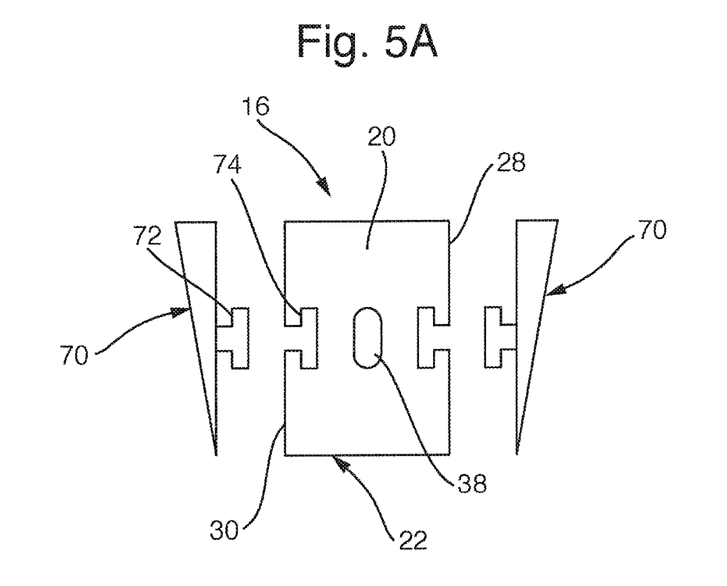
FIG. 5A shows a cage assembly comprising a cage body and width adjustment members.
Figure 5B:
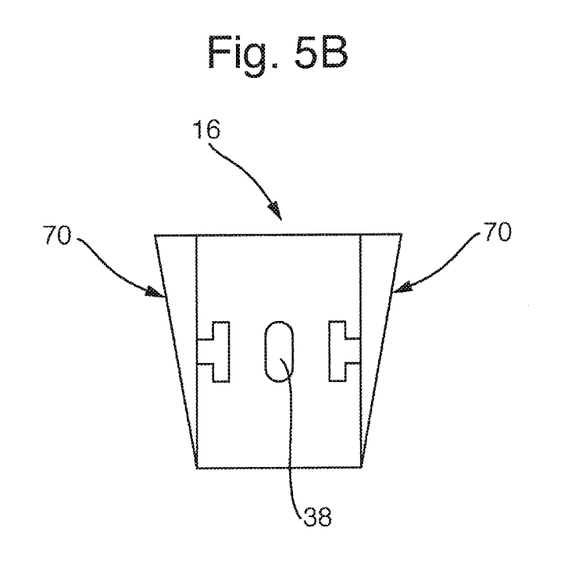
FIG. 5B shows the cage assembly after the width adjustment members have been attached to the cage body.

FIGS. 5A and 5B show an embodiment in which the cage assembly comprises width adjustment members 70. These figures show an end view of the cage body 16 when looking towards the head 38 of the cage body 16. As shown in FIG. 5A, the cage body 16 may have a substantially square or rectangular cross-section, as viewed from the end. Each width adjustment member 70 may have a tapered cross-section, as viewed from the end of the cage body 16. Each width adjustment member 70 has a male key 72 for interlocking with a female key 74 on each side 28, 30 of the cage body. Each female key 74 may be a longitudinal slotted channel extending along the axial length of the cage body 16. The male key 72 may then be slid into this channel so as to interlock the width adjustment member 70 with the cage body 16, as shown in FIG. 5B, such that the width adjustment member 70 cannot be moved laterally away from the cage body 16. It will therefore be appreciated that the width adjustment members 70 alter the total width of the cage assembly to the width at which the bone portions 10, 14 are desired to be spaced apart. This configuration enables the user to keep an inventory of different sized width adjustment members 70 such that different widths may be created from the same cage body 16 and simply by using different width adjustment members 70. It is also contemplated that the sides 28, 30 of the cage body 16 may be tapered in addition to, or as an alternative to, the width adjustment members 70 being tapered. In configurations in which the sides 28, 30 of the cage body 16 are tapered, the width adjustment members 70 may not be tapered.

The invention claimed is:

1. A cage assembly for implanting between and securing together two portions of bone in a tibial tuberosity advancement, the cage assembly comprising:
   an elongated cage body having a first end, a second end, opposing sides, a top and a bottom, the cage body for placement between said two portions of bone such that each side contacts one of said portions of bone so as to maintain a space between the portions of bone; and
   a securing member;
   wherein the first end of the cage body and the securing member are configured to be engagable with each other so as to interlock in a manner that prevents the securing member from moving longitudinally away from the cage body;
   wherein the securing member is arrangable, when interlocked with the cage body, such that it has a portion which extends laterally outwards beyond each opposing side of the cage body for use in attaching said securing member to said portions of bone;
   wherein the securing member and cage body are releasably engagable such that they may be repeatedly interlocked with and disengaged from each other; and
   wherein the securing member is rotatable up to at least ±25 degrees relative to said cage body when interlocked with the cage body.

2. The cage assembly of claim 1, wherein the cage body comprises a neck portion that extends to a head at the first end of the cage body, wherein the securing member comprises an aperture, and wherein the head and aperture are sized and configured such that the aperture may be placed over the head and onto the neck when the securing member is arranged at a first orientation and the securing member may then be rotated about a longitudinal axis of the neck to a second orientation such that the head of the cage body prevents the securing member from being pulled back over the head and away from the cage body.

3. The cage assembly of claim 2, wherein the securing member and cage body are profiled such that when the securing member is progressively rotated from the first orientation to the second orientation a surface of the securing member engages with a surface of the head, or a surface of another part of the cage body, such that the friction between the two surfaces progressively increases.

4. The cage assembly of claim 2, wherein each said side of the cage body tapers where said side contacts a respective one of said portions of bone.

5. The cage assembly of claim 1, wherein each portion of the securing member that extends laterally outwards beyond each opposing side of the cage body when the securing member is interlocked with the cage body comprises an opening through which the securing member is screwed or pinned to the bone portions in use.

6. The cage assembly claim 1, wherein the first end of the cage body has a first substantially planar surface and the second end of the cage body has a second substantially planar surface, the first and second planar surfaces being angled relative to each other.

7. The cage assembly of claim 6, wherein the planar surfaces are angled so as to converge towards each other in the direction from the top of the cage body towards the bottom of the cage body.

8. The cage assembly of claim 6, wherein the substantially planar surface at the first end of the cage body is substantially perpendicular to the top and bottom of the cage body.

9. The cage assembly of claim 1, wherein the top and/or bottom of the cage body is a single continuous rectangle over at least half of the length of the cage body.

10. The cage assembly of claim 1, wherein the cage body comprises a box portion arranged towards the first end and a tail portion arranged towards the second end, wherein the tail portion comprises a substantially planar vane member that is connected to the box portion by one or more rod member so as to be spaced apart from the box portion.

11. The cage assembly of claim 10, wherein the tail portion comprises one or more additional substantially planar vane members, wherein the vane members are connected together in the tail portion by one or more rod member between each adjacent pair of vane members such that the adjacent vane members are spaced apart from each other.

12. A method of performing a tibial tuberosity advancement using the cage assembly of claim 1, the method comprising:
inserting the cage body in a space between a tibial tuberosity and another portion of a tibia bone, wherein the cage body and securing member are interlocked with each other; and
screwing or pinning said securing member to said tibial tuberosity and to said another portion of the tibia.

13. A cage assembly for implanting between and securing together two portions of bone in a tibial tuberosity advancement, the cage assembly comprising:

an elongated cage body having a first end, a second end, opposing sides, a top and a bottom, the cage body for placement between said two portions of bone such that each side contacts one of said portions of bone so as to maintain a space between the portions of bone; and
a securing member;
wherein the first end of the cage body and the securing member are configured to be engagable with each other so as to interlock in a manner that prevents the securing member from moving longitudinally away from the cage body;
wherein the securing member is arrangable, when interlocked with the cage body, such that it has a portion which extends laterally outwards beyond each opposing side of the cage body for use in attaching said securing member to said portions of bone;
wherein the securing member and cage body are releasably engagable such that they may be repeatedly interlocked with and disengaged from each other;
wherein the securing member is rotatable relative to said cage body when interlocked with the cage body; and
wherein at least one of:
a) the cage assembly comprises a plurality of said securing members, the securing members being of different sizes such that in use each securing member can be attached to said portions of bone at different locations and at different distances from the cage body; and
b) the first end of the cage body has a first substantially planar surface and the second end of the cage body has a second substantially planar surface, the first and second planar surfaces being parallel to each other and perpendicular to the top and bottom.

14. A cage assembly for implanting between and securing together two portions of bone in a tibial tuberosity advancement, the cage assembly comprising:
an elongated cage body having a first end, a second end, opposing sides, a top and a bottom, the cage body for placement between said two portions of bone such that each side contacts one of said portions of bone so as to maintain a space between the portions of bone; and
a securing member configured to interlock with the cage body and for securing to said portions of bone;
wherein at least one of:
a) the cage body comprises a box portion arranged towards the first end and a tail portion arranged towards the second end, wherein the tail portion comprises a substantially planar vane member that is connected to the box portion by one or more rod members so as to be spaced apart from the box portion, and wherein the first end of the cage body has a first substantially planar surface and the vane member is substantially planar, the planar surface of the vane member being angled relative the first planar surface so as to converge towards each other in the direction from the top of the cage body towards the bottom of the cage body;
b) wherein the cage body comprises a box portion arranged towards the first end and a tail portion arranged towards the second end, wherein the tail portion comprises a substantially planar vane member that is connected to the box portion by one or more rod members so as to be spaced apart from the box portion, wherein either:
only a single rod member connects the vane member to the box portion, the single rod member being located substantially centrally between the top and bottom of the cage body; or a rod member connects the vane member to the box portion at each of the four corners of the cage body arranged between the top, bottom and sides of the cage body c) wherein each side wall is recessed inwards between the top and bottom of the cage body such that when the cage body is positioned between the bone portions only upper and lower regions of the side walls contact the bone portions and not the central regions of the side walls; and d) wherein the assembly comprises at least one width adjustment member for altering the width of the cage, wherein a side of the cage body and said width adjustment member are configured to be engagable with each other so as to interlock in a manner that prevents the width adjustment member moving laterally away from the cage body.

15. The cage assembly of claim 14, wherein each side of said cage body is configured to be engagable with and interlock with one of said width adjustment members.

16. The cage assembly of claim 14, wherein the width adjustment member or the side of the cage body comprises a male key, and the side of the cage body or width adjustment member respectively comprises a female key for interlocking with the male key.

17. The cage assembly of claim 14, wherein the width adjustment member or the side of the cage body comprises a slot, and the side of the cage body or width adjustment member respectively comprises a protrusion for interlocking with the slot.

18. The cage assembly of claim 17, wherein the slot extends longitudinally along the cage body or width adjustment member and the protrusion is configured to be slid longitudinally into the slot so as to interlock the cage body with the width adjustment member.

19. The cage assembly of claim 14, wherein at least one of the cage body and the securing member is made of a polymer and the polymer is a bio-absorbable polymer that will be absorbed into an animal body over time when implanted within the animal body.

20. A cage assembly for implanting between and securing together two portions of bone in a tibial tuberosity advancement, the cage assembly comprising:

an elongated cage body having a first end, a second end, opposing sides, a top and a bottom, the cage body for placement between said two portions of bone such that each side contacts one of said portions of bone so as to maintain a space between the portions of bone; and a securing member;

wherein the first end of the cage body and the securing member are configured to be engagable with each other so as to interlock in a manner that prevents the securing member from moving longitudinally away from the cage body;

wherein the securing member is arrangable, when interlocked with the cage body, such that it has a portion which extends laterally outwards beyond each opposing side of the cage body for use in attaching said securing member to said portions of bone; and wherein the cage body comprises a neck portion that extends to a head at the first end of the cage body, wherein the securing member comprises an aperture, and wherein the head and aperture are sized and configured such that the aperture may be placed over the head and onto the neck when the securing member is arranged at a first orientation and the securing member may then be rotated about a longitudinal axis of the neck to a second orientation such that the head of the cage body prevents the securing member from being pulled back over the head and away from the cage body.

21. The cage assembly of claim 20, wherein each said side of the cage body tapers where said side contacts a respective one of said portions of bone.

* * * * *